United States Patent [19]

Wakasugi et al.

[11] Patent Number: 5,414,139
[45] Date of Patent: May 9, 1995

[54] PROCESS FOR THE MANUFACTURE OF MONOCHLOROACETALDEHYDE TRIMER AND CHLORAL

[75] Inventors: Takashi Wakasugi; Tadashi Miyakawa; Fukuichi Suzuki, all of Fukushima, Japan

[73] Assignee: Kureha Chemical Industry Co., Ltd., Tokyo, Japan

[21] Appl. No.: 214,123

[22] Filed: Mar. 15, 1994

[30] Foreign Application Priority Data

Apr. 21, 1993 [JP] Japan ................... 5-117811

[51] Int. Cl.$^6$ .................... C07C 45/53; C07C 45/61
[52] U.S. Cl. ..................... 568/466; 568/490; 568/495
[58] Field of Search ............... 568/490, 488, 495, 466

[56] References Cited

U.S. PATENT DOCUMENTS

| | | | |
|---|---|---|---|
| 2,768,173 | 10/1955 | Wohlers et al. | 568/488 |
| 2,942,031 | 6/1960 | Kundiger et al. | 568/488 |
| 3,381,036 | 4/1968 | Clark et al. | 568/490 |
| 5,008,462 | 4/1991 | Ishizuka et al. | 568/488 |

FOREIGN PATENT DOCUMENTS 368613 11/1989 European Pat. Off. .

OTHER PUBLICATIONS

Chemical Abstracts, vol. 116, No. 11, 16 Mar. 1992, Columbus, Ohio, US; Abstract No. 106244, Wakasugi T et al "Preparation of chloroacetaldehyde cyclic trimer and its depolymerization"Abst.
Database WPI Section Ch, Week 8543, Derwent Publications Ltd., London, GB; Class E16, AN 85-266705 & JP-A-60 178 839 (Daicel Chem Ind KK (Dail) Daicel Chem Ind Ltd 12 Sep. 1985 Abstract.
Database WPI Section Ch, Week 9336, Derwent Publications Ltd., London, GB; Class E13, AN 92-285422 & JP-A-5 202 026 (Kureha Chem Ind Co Ltd) 10 Aug. 1993 Abstract.

*Primary Examiner*—Werren B. Lone
*Attorney, Agent, or Firm*—Burgess, Ryan & Wayne

[57] ABSTRACT

A process for manufacturing monochloroacetaldehyde trimer and chloral together by effectively utilizing a raw material acetaldehyde or para-aldehyde. The process comprises a step of chlorinating acetaldehyde or para-aldehyde to produce a chlorinated liquid of which the major component is monochloroacetaldehyde, a step comprising adding chloral to said chlorinated liquid and distilling the mixture to obtain a fraction of which the major components are monochloroacetaldehyde and chloral, a step of trimerizing monochloroacetaldehyde by reacting said fraction in the presence of a trimerization catalyst and separating the MCA trimer by filtration, and a step of chlorinating other fractions from said distillation step and the filtrate from said trimerization step to produce chloral. According to this process all raw material aldehydes and components derived from aldehydes which have not been consumed for the production of MCA trimer can be easily converted into chloral which is useful as an industrial chemical. The process is also free from the problem of the waste water treatment.

4 Claims, No Drawings

PROCESS FOR THE MANUFACTURE OF MONOCHLOROACETALDEHYDE TRIMER AND CHLORAL

BACKGROUND OF THE INVENTION

1. Field of the Invention

The present invention relates to a process for manufacturing monochloroacetaldehyde trimer together with chloral.

2. Description of the Background Art

Monochloroacetaldehyde (hereinafter abbreviated as MCA) is a compound useful as a raw material for the synthesis of organic compounds such as drugs and agricultural chemicals. Because this compound is extremely unstable and polymerizes very easily, it has been difficult to store it as is for a long period of time. Because of this, MCA is stored as an aqueous solution of about 40%. It has beer found that MCA can be stored stably, if trimerized into a trimer and stored as the trimer, and the trimer can be regenerated into high purity MCA. A process for the manufacture of MCA trimer has been proposed by Japanese Patent Laid-open (kokai) No. 223575/1990. This process comprises chlorinating acetaldehyde or para-aldehyde to a degree at which MCA can be obtained at a highest concentration, removing low-boiling point components by bubbling an inert gas such as nitrogen gas, dissolving the chlorinated liquid containing MCA as a major component, and trimerizing the MCA in the presence of high concentrated sulfuric acid.

In this process the chlorination of the raw material acetaldehyde or para-aldehyde is carried out under the conditions which can bring about the highest MCA concentration, while suppressing production of dichloroacetaldehyde (hereinafter abbreviated as DCA). However, the amount of acetaldehyde unreacted is increased when reacted under such conditions. Separation of this unreacted acetaldehyde by distillation accompanies production of high-boiling point components due to condensation reactions among aldehyde molecules, making it difficult to reclaim acetaldehyde which has not been chlorinated. The yield of MCA by distillation is also reduced. Furthermore, this process has another problem in that it requires washing the solution containing MCA trimer with water in order to remove concentrated sulfuric acid which is used as a catalyst for trimerizing MCA after removal of non-chlorinated acetaldehyde. When the solution containing MCA trimer is washed with water, non-trimerized aldehydes, which are abundantly soluble in water, are transferred to the water phase. It is almost impossible to reclaim the aldehydes transferred to the water phase. The utilization of raw material acetaldehyde and para-aldehyde in this process is thus extremely low.

In view of this situation, the present inventors have undertaken further studies in order to more effectively manufacture MCA trimer, and found that this objective can be achieved by a process comprising chlorinating acetaldehyde or para-aldehyde to a non-chlorinated acetaldehyde concentration of 5% or less, distilling the produced MCA in the presence of chloral, trimerizing the MCA, and converting the non-trimerized acetaldehydes into chloral.

SUMMARY OF THE INVENTION

Accordingly, an object of the present invention is to provide a process for manufacturing MCA trimer by effectively utilizing raw material acetaldehyde or para-aldehyde.

Another object of the present invention is to provide a process for manufacturing MCA trimer by effectively utilizing raw material acetaldehyde or para-aldehyde by the coproduction of MCA trimer and chloral.

Still another object of the present invention is to provide a process for manufacturing MCA trimer by effectively utilizing raw material acetaldehyde or para-aldehyde by the coproduction of MCA trimer and chloral using a trimerization catalyst which can be readily separated.

These objects of the present invention can be achieved by a process of manufacturing MCA trimer and chloral comprising, a step of chlorinating acetaldehyde or para-aldehyde to produce a chlorinated liquid of which the major component is MCA, a step comprising adding chloral to said chlorinated liquid and distilling the mixture to obtain a fraction of which the major components are MCA and chloral, a step of trimerizing MCA by reacting said fraction in the presence of a trimerization catalyst and separating the MCA trimer by filtration, and a step of chlorinating other fractions from said distillation step and the filtrate from said trimerization step to produce chloral.

Other and further objects, features and advantages of the present invention will appear more fully from the following description.

DETAILED DESCRIPTION OF THE INVENTION AND PREFERRED EMBODIMENTS

MCA used for the trimerization reaction in the present invention can be obtained by the chlorination of para-aldehyde or acetaldehyde. When the chlorination reaction is carried out to a chlorination degree (the average number of chlorine atoms bonded to 1 mole of acetaldehyde molecule) of about 1.1 to 1.3, a chlorinated liquid containing about 50% of MCA, about 20% of DCA, and about 3% of acetaldehyde can be obtained.

If this chlorinated liquid is distilled after the addition of chloral, an unreacted chlorine gas is first distilled, following which a fraction of about 80° to 87° C., which is a liquid product containing MCA, DCA and chloral at an approximately specific ratio, can be obtained. The distillation residue is a chloral solution containing MCA and DCA, in which the ratio of MCA to DCA is smaller than that of original liquid. Production of high-boiling point components is very small. The amount of chloral added before the distillation is 40 to 150%, and preferably 50 to 120%, of that of the chlorinated liquid.

Distillation of the chlorinated liquid without the addition of chloral produces high-boiling point components, which conspicuously color the distillation residue. These high-boiling point components must be disposed as waste materials, resulting in loss of the chlorination raw material.

The trimerization reaction can be carried out by adding a trimerization catalyst to said chlorinated liquid fraction at a temperature at which the mixture is not frozen, preferably at 50° C. or lower, and more preferably at 0° to 45° C. If the reaction temperature is above 50° C., the production of high-boiling point components is promoted; if it is below 0° C., the reaction is retarded.

As a trimerization catalyst, a catalyst which catalyzes the trimerization reaction and remains as a solid after the trimerization reaction so that it can be removed by filtration can be used. A catalyst which does not interfere with the chlorination reaction of the liquid after the separation of the MCA trimer produced can also be used. Metallic tin, metallic zinc, zeolite and the like can be given as examples of the catalysts which remain as solid after the trimerization reaction and can be removed by filtration. Heteropoly acids, Lewis acids and the like can be given as the catalysts which do not interfere with the chlorination reaction. Among these, metallic tin and metallic zinc are particularly preferred, because they can selectively trimerize MCA and exhibit almost no action on DCA which is present together with MCA in the reaction solution.

After the reaction, the catalyst which can be filtered is removed by filtration when MCA trimer is deposited as crystals, the catalyst is removed after the crystals have been dissolved with heating. If the reaction solution is allowed to stand at a low temperature, the MCA trimer deposites as crystals.

The residual solution obtained after the separation of the MCA trimer is a chloral solution containing a small amount of MCA which has not been trimerized and DCA. If this chloral solution is combined with the above-mentioned initial distillate and distillation residue, and the mixture is chlorinated, almost all raw materials for the chlorination reaction, which have not been trimerized, can be converted into chloral with minimal loss.

The chlorination of the residue after the separation of the trimer is carried out with the addition of a chlorination catalyst, if necessary. After the completion of the chlorination reaction, the chlorination catalyst is removed from the reaction mixture together with the trimerization catalyst, if the latter has not been removed yet, to obtain a chloral product.

According to the process of the present invention, about as much as 15% of the raw materials, para-aldehyde and acetaldehyde, can be converted into MCA trimer and the remaining raw materials can be converted into chloral.

As illustrated above, according to the process of the present invention almost all raw material aldehydes and components derived from aldehydes which have not been consumed for the production of MCA trimer can be easily converted into chloral which is useful as an industrial chemical. In addition, the process produces almost no high-boiling point materials. Thus, the process of the present invention can effectively utilize para-aldehyde and acetaldehyde which are the raw materials. Furthermore, this process have no problem relating to the waste water treatment as in the case of conventional processes.

Other features of the invention will become apparent in the course of the following description of the exemplary embodiments which are given for illustration of the invention and are not intended to be limiting thereof.

EXAMPLES

EXAMPLE 1

(Preparation of Chlorinated Liquid)

140 g of para-aldehyde and 1.4 ml of water were charged into a 500 ml three-necked flask equipped with a stirrer, a reflux condenser and a thermometer, and the solution was maintained at 10° C. Chlorine gas was introduced into this solution at a rate of 200 ml/min to initiate the chlorination reaction. Thereafter, chlorine gas was introduced at a rate of 200 to 700 ml/min for 8.5 hours, while maintaining the temperature at 6°±3° C., to obtain 300 g of a chlorinated solution. Chlorine gas produced by the chlorination reaction was absorbed by an aqueous solution of sodium hydroxide.

(Concentration by Distillation)

150 g of chloral was added to the chlorinated solution and the mixture was distilled under atmosphere. 120 g of a fraction distilled at 80° to 87° C. was obtained. This fraction was confirmed by gas chromatography analysis to consist of 43% of MCA, 11% of DCA, 34% chloral, 2% of acetaldehyde, and a trace amount of high-boiling point components. The amount of the fractionated MCA was 35% of the total amount of MCA in the chlorinated liquid used.

(Synthesis of Trimer)

Synthesis of MCA trimer was carried out in a 300 ml three-necked flask equipped with a stirrer and a thermometer. 2.6 g of metallic tin (5% for MCA) was added to 120 g of the distillation fraction having the above composition, and the reaction was carried out at 20° C. for 3 hours. After completion of the reaction, the deposited crystals were dissolved at 30° C. and the metallic tin was removed by filtration. The filtrate thus obtained was allowed to stand still at 10° C. to deposit crystals. 40 g of white crystals of MCA trimer was obtained by filtration. This MCA trimer had a purity of 98.5% and the yield was 76% based on the MCA in the distillation fraction. The metallic tin was reclaimed with no loss in mass and could be recycled without no activation treatment.

(Synthesis of Chloral)

The initial distillate distilled at 79° C. or below and high-boiling point components of 88° C. or higher, obtained in the distillation of the chlorinated liquid, were combined with the filtrate obtained by the separation of the trimer crystals. The mixture was chlorinated at 50° to 60° C. into chloral.

As a result, 16% of the raw material para-aldehyde was converted into MCA trimer and 84% into chloral, with the utilization of the para-aldehyde being 100%.

Comparative Example (Preparation of Chlorinated Liquid)

140 g of para-aldehyde and 1.4 ml of water were charged into a 500 ml three-necked flask equipped with a stirrer, a reflux condenser and a thermometer, and the solution was maintained at 10° C. Chlorine gas was introduced into this solution at a rate of 200 ml/min to initiate the chlorination reaction. Thereafter, chlorine gas was introduced at a rate of 200 to 700 ml/min for 8.5 hours, while maintaining the temperature at 6°±3° C., to obtain 300 g of a chlorinated solution. Chlorine gas produced by the chlorination reaction was absorbed by an aqueous solution of sodium hydroxide.

(Purification by Distillation)

The chlorinated solution was distilled under atmosphere. The unreacted chlorine gas and acetaldehyde were reclaimed, following which 90 g of a fraction distilled at 82° to 89° C., which contained 82% of MCA, was obtained. The distillation residue was colored in brown.

(Synthesis of trimer)

Synthesis of MCA trimer was carried out in a 300 ml three-necked flask equipped with a stirrer and a thermometer. 90 g of the above fraction was added to 200 ml of hexane and cooled to −20° C., whereupon 9.8 ml of 96% concentrated sulfuric acid (20% for the distillate) was slowly added in 20 minutes. This mixture was stirred for 1 hour while maintaining the temperature at −10° C. to effect the trimerization reaction.

After the completion of the reaction, 500 ml of diethyl ether was added to dissolve deposited crystals. The organic layer was washed with water and 10% aqueous solution of sodium hydroxide, and dried over magnesium sulfate. The solvent was evaporated under reduced pressure (2.67 kPa) to obtain 38 g of crystals of MCA trimer with a purity of 99.5%. The yield of the MCA trimer was 15% based on the raw material paraaldehyde and 51% based on the distilled fraction.

The chlorinated liquid distillation residue was colored and could not be converted into useful chloral. Furthermore, aldehyde components not converted into the MCA trimer was transferred to the water layer during washing with water and it was difficult to reclaim them.

EXAMPLE 2

In a 300 ml three-necked flask equipped with a stirrer and a thermometer was charged 100 g of a distillation fraction consisting of 46% of MCA, 13% of DCA, 32% of chloral, and 1% of acetaldehyde and high-boiling point components, obtained in the same manner as in Example 1. 9.2 g of 12 tungstophosphate (20% for MCA) was added to react at 25° C. for 3 hours. After completion of the reaction, the reaction mixture was heated to 30° C. to dissolve the deposited crystals, and then allowed to stand still at 10° C. The crystals deposited were collected by filtration to obtain 36 g of white crystals (purity 99.0%) of MCA trimer. The yield of the MCA trimer was 71% based on the MCA in the distillation fraction. The crystals were recrystallized from methanol to obtain 25 g of white crystals of MCA trimer with a purity of 99.5%.

The initial distillate distilled at 79° C. or below and high-boiling point components of 88° C. or higher, obtained in the distillation of the chlorinated liquid, were combined with the filtrate obtained by the separation of the trimer crystals, and the mixture was chlorinated into chloral.

EXAMPLE 3

In a 300 ml three-necked flask equipped with a stirrer and a thermometer was charged 100 g of a distillation fraction consisting of 43% of MCA, 11% of DCA, 36% of chloral, and 1% of acetaldehyde and high-boiling point components, obtained in the same manner as in Example 1. 0.43 g of antimony trichloride (1% for MCA) was added to react at 25° C. for 2 hours. After completion of the reaction, the reaction mixture was heated to 30° C. to dissolve the deposited crystals, and then allowed to stand still at 10° C. The crystals deposited were collected by filtration to obtain 31 g of white crystals (purity 98.8%) of MCA trimer. The yield of the MCA trimer was 71% based on the MCA in the distillation fraction. The crystals were recrystallized from methanol to obtain 25 g of white crystals of MCA trimer with a purity of 99.5%.

The initial distillate distilled at 79° C. or below and high-boiling point components of 88° C. or higher, obtained in the distillation of the chlorinated liquid, were combined with the filtrate obtained by the separation of the trimer crystals, and the mixture was chlorinated into chloral.

Obviously, numerous modifications and variations of the present invention are possible in light of the above teachings. It is therefore to be understood that within the scope of the appended claims, the invention may be practiced otherwise than as specifically described herein.

What is claimed is:

1. A process of manufacturing monochloroacetaldehyde trimer together with chloral comprising,
   (a) chlorinating acetaldehyde or paraldehyde with a chlorinating agent to produce a chlorinated liquid of which the major component ms monochloroacetaldehyde,
   (b) adding chloral to said chlorinated liquid and distilling the mixture to obtain a fraction of which the major components are monochloroacetaldehyde and chloral,
   (c) trimerizing monochloroacetaldehyde by reacting said fraction in the presence of a trimerization catalyst and separating the monochloroacetaldehyde trimer by filtration, and
   (d) chlorinating other fractions from said distillation step and the filtrate from said trimerization step to produce chloral.

2. The process according to claim 1, wherein the amount of chloral added to the chlorinated liquid before distillation is 40 to 150%.

3. The process according to claim 1, wherein the trimerization catalyst is at least one catalyst selected from metallic tin, metallic zinc, and zeolite.

4. The process according to claim 1, wherein the trimerization catalyst is a heteropoly acid or a Lewis acid.

* * * * *